US006861072B1

United States Patent
Alaux et al.

(10) Patent No.: US 6,861,072 B1
(45) Date of Patent: Mar. 1, 2005

(54) PHARMACEUTICAL COMPOSITION WITH GASTRIC RESIDENCE AND CONTROLLED RELEASE

(75) Inventors: Gérard Alaux, Beynes (FR); Frédéric Andre, Antony (FR); Alain Cuine, Saint Fargeau-Ponthierry (FR); Gareth Lewis, Dourdan (FR)

(73) Assignee: Sanofi-Synthelabo, Paris (FR)

(*) Notice: Subject to any disclaimer, the term of this patent is extended or adjusted under 35 U.S.C. 154(b) by 0 days.

(21) Appl. No.: 09/807,573

(22) PCT Filed: Oct. 12, 1999

(86) PCT No.: PCT/FR99/02443

§ 371 (c)(1),
(2), (4) Date: Jun. 4, 2001

(87) PCT Pub. No.: WO00/23045

PCT Pub. Date: Apr. 27, 2000

(30) Foreign Application Priority Data

Oct. 16, 1998 (FR) .............................. 98 12977

(51) Int. Cl.⁷ ............................. A61K 9/24; A61K 9/00; A61K 9/20; A61K 9/22; A61K 9/46
(52) U.S. Cl. ...................... 424/472; 424/400; 424/464; 424/465; 424/466; 424/468; 424/469
(58) Field of Search ................................ 424/400, 464, 424/465, 466, 468, 469, 472, 473, 486, 487, 488

(56) References Cited

U.S. PATENT DOCUMENTS

| 5,651,985 A | * | 7/1997 | Penners et al. |
| 6,120,803 A | * | 9/2000 | Wong et al. |
| 6,149,940 A | * | 11/2000 | Maggi et al. ............... 424/472 |

FOREIGN PATENT DOCUMENTS

| EP | 669 129 | | 2/1995 | |
| FR | 2 762 213 | | 4/1997 | |
| WO | 96/29054 | | 9/1996 | |
| WO | 97/47285 | | 12/1997 | |
| WO | WO 97/47285 | * | 12/1997 | |
| WO | WO 98/08515 | * | 3/1998 | ......... A61K/31/505 |
| WO | 98/11879 | | 3/1998 | |

OTHER PUBLICATIONS

Derwent Patent Abstract No. 199849.

* cited by examiner

Primary Examiner—Thurman K. Page
Assistant Examiner—Simon J. Oh
(74) Attorney, Agent, or Firm—Paul E. Dupont; Michael D. Alexander

(57) ABSTRACT

The invention concerns a pharmaceutical composition with gastric residence and controlled release, characterized in that it comprises two or three layers and contains (a) an active principle associated with a excipient modifying its release; (b) a system generating carbon dioxide in a swelling polymer hydrophilic matrix; (a) and (b) capable of being included in a common layer or in separate layers.

29 Claims, 1 Drawing Sheet

PHARMACEUTICAL COMPOSITION WITH GASTRIC RESIDENCE AND CONTROLLED RELEASE

The present invention relates to controlled-release pharmaceutical compositions with gastric residence.

Attempts are most frequently made to administer medicinal products orally. However, oral administration is occasionally made difficult when the active principle is of low bioavailability.

The term "bioavailability" means herein the fraction of active principle which is absorbed from its pharmaceutical form and which arrives in the plasma.

Other active principles are absorbed and may thus be administered orally, but their absorption is incomplete and occasionally irregular. Some other active principles are absorbed well from fast-release pharmaceutical forms, the active principle then being released in less than half an hour, but are less well absorbed from sustained-release pharmaceutical forms.

Such a low and irregular bioavailability may be the result of several factors. Among these, mention may be made of low solubility or very slow dissolution of the active principle, chemical or enzymatic degradation of the active principle in the gastrointestinal tract or slow or incomplete absorption of the active principle.

Specifically, a certain number of active principles, although being sufficiently soluble, are poorly absorbed in the colon or less well absorbed at this level than in the upper sections of the small intestine, namely the duodenum, the jejunum and the ileum.

Furthermore, a sustained-release form is useful for many medicinal products, for example to allow a less frequent administration: once a day instead of twice a day, or twice a day instead of 3 times a day.

When the active principle is absorbed slowly or incompletely in the lower regions of the gastrointestinal tract, it becomes difficult to design a sustained-release form, which should typically release the active principle over 12 to 16 hours. The problem becomes all the more difficult if there is a window of absorption, i.e. if the active principle is absorbed well only in a portion of the gastrointestinal tract. For example, the active principle may be absorbed well only in the duodenum and the jejunum. Specifically, a sustained-release pharmaceutical form requires a release time of at least 8 hours, which is not achieved in the case of an active principle which is absorbed essentially in the upper sections of the small intestine. This is the problem which the Applicant proposes to solve.

The present invention is thus directed toward slowing down the speed of gastrointestinal transit and thus of increasing the time available for absorption in the upper sections of the small intestine and more specifically the duodenum, the jejunum and the ileum, while at the same time controlling the release profile.

The invention thus consists of a pharmaceutical composition with gastric residence, characterized in that it comprises two or three layers and in that it comprises.

(a) an active principle combined with an excipient which modifies its release,
(b) a carbon dioxide-generating system in a swelling hydrophilic polymer matrix.

The two- or three-layer tablets made from the various combinations of (a) and (b) form part of the invention, (a) and (b) possibly being included in the same layer [(a)+(b)] or in separate layers [(a)] and [(b)]. The redundant layers [(a)], [(b)] or [(a)+(b)] in the same tablet may have different compositions and dimensions.

Compositions which also form part of the invention are compositions with gastric residence containing two or three layers comprising (a) and (b), characterized in that they comprise a soluble and/or erodable layer. The tablet may thus comprise a layer [(a)+(b)] and a soluble and/or erodable layer to give a two-layer tablet, or alternatively a soluble and/or erodable layer coated with two outer layers [(a)+(b)] to give a three-layer tablet.

This embodiment makes it possible, like all the compositions according to the invention, to obtain a gradual increase in the contact area between the tablet and the liquids contained in the stomach, so as to tend toward a zero-order dissolution profile, that is to say a controlled-release profile.

The compositions according to the invention are characterized in that, on contact with the gastric juices, the layer(s) [(b)] or [(a)+(b)] increase in volume by virtue of the swelling of the hydrophilic polymer matrix and the immediate production of carbon dioxide. In this way, flotation is obtained quickly and the gastric residence time obtained is large.

The pharmaceutical compositions according to the invention may be useful, for example, for benzamides and $\alpha_1$-antagonists, and also the following active principles: captopril, furosemide, ursodeoxycholic acid, amoxicillin, (+)-$\alpha$-aminomethyl-2-methoxysulfonamidobenzenemethanol (disclosed in patent application EP 842 148 in Example 3.6) or 3'-(2-amino-1-hydroxyethyl)-4'-fluoromethane-sulfonanilide (NS 49).

The benzamides are, in particular, metoclopramide, veralipride, alizapride, clebopride and more particularly amisulpride, tiapride and sulpiride, and salts thereof.

The $\alpha_1$-antagonists are, in particular, terazosine and alfuzosine and salts thereof, in particular alfuzosine hydrochloride. They are intended especially for treating benign hypertrophy of the prostate.

Captopril is used in particular for treating hypertension, furosemide is used as a diuretic, amoxicillin and its salts are used as antibiotics, and ursodeoxycholic acid and its salts are used for treating cholelithiasis, liver disorders and syphilis.

For the purposes of the present invention, the various enantiomers or diastereoisomers of the various active principles or families of active principles (benzamides, $\alpha_1$-antagonists) are also covered, including mixtures thereof, in particular racemic mixtures thereof, and also salts thereof.

Among the active principles that are more particularly suitable for the compositions according to the invention, mention may be made of amisulpride (D)-tartrate, (S)-(–)-amisulpride, (S)-(–)-amisulpride (D)-tartrate, tiapride hydrochloride, alfuzosine hydrochloride and 3'-(2-amino-1-hydroxyethyl)-4'-fluoromethanesulfonanilide hydrochloride.

Figure 1:
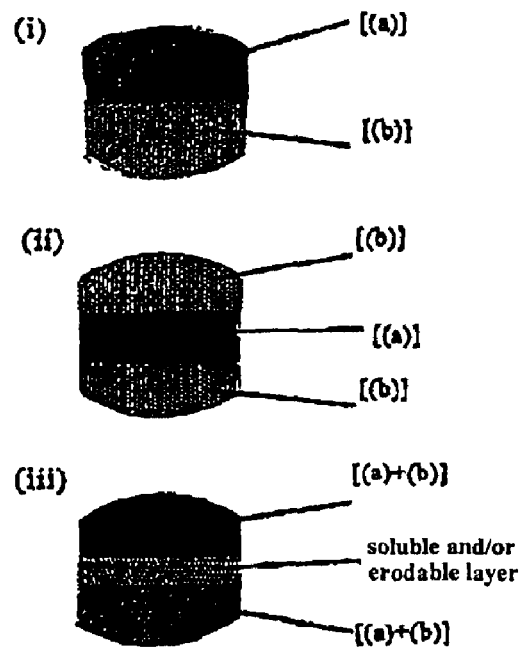
FIG. 1 shows three embodiments of the invention with various arrangements of (a) and (b).

The main function of the carbon dioxide-generating system is to form carbon dioxide in the form of bubbles. These bubbles contribute toward rapidly bringing and then maintaining the pharmaceutical composition of the invention at the surface of the liquids contained in the stomach.

A carbon dioxide-generating system which is suitable in a pharmaceutical composition according to the invention generally comprises at least one carbon dioxide-generating agent. The carbon dioxide-generating agent is usually an alkali metal carbonate or an alkaline-earth metal carbonate, such as calcium carbonate, or an alkali metal bicarbonate, preferably sodium bicarbonate.

Such a carbon dioxide-generating system, consisting solely of a carbon dioxide-generating agent, does not begin to form carbon dioxide bubbles until it has been placed in contact with a medium at acidic pH, generally that of the stomach.

In order to accelerate the formation of carbon dioxide bubbles and thus improve the flotation of the pharmaceutical composition with gastric residence of the invention, it is preferred to use a pH-independent carbon dioxide-generating system. Such a system may comprise a carbon dioxide-generating agent such as those mentioned above, along with at least one acidic compound chosen from the group consisting of monocarboxylic acids such as lactic acid, polycarboxylic acids and partial salts of polycarboxylic acids. Acidic compounds which may be mentioned more particularly include tartaric acid, maleic acid, malonic acid, malic acid, fumaric acid, succinic acid, adipic acid and citric acid and partial salts thereof, such as monosodium citrate.

In such a carbon dioxide-generating system, the content of acidic compound is generally chosen such that the number of moles of the said acidic compound relative to the number of moles of the said carbon dioxide-generating agent is from 0.7 to 1.4 times the stoichiometry.

However, if the active principle or any other component forming part of the formulation of the composition according to the invention is of basic nature, it may be consequently necessary to increase the content of acidic compound.

The hydrophilic polymers which are suitable for forming a swelling hydrophilic polymer matrix may be chosen from:

natural polysaccharides such as alginates, xanthan gum, guar gum, gum arabic or carob gum,
semi-synthetic polysaccharides, in particular cellulose derivatives such as methylhydroxyethyl-cellulose, cellulose, carboxymethylcellulose and its salts such as sodium carboxymethylcellulose or calcium carboxymethylcellulose, hydroxypropylcellulose or hydroxypropylmethylcellulose, or
synthetic hydrophilic polymers such as
polyvinylpyrrolidones,
polymers derived from acrylic acid and methacrylic acid and salts thereof, such as polyacrylates, in particular those sold under the brand name Carbopol®, or
aminoacid polymers such as polylysines.

Among the natural polysaccharides that are preferred are alginates and xanthan gum.

Among the semi-synthetic polysaccharides that are preferred are hydroxypropylcellulose and hydroxypropylmethylcellulose.

The swelling hydrophilic polymer matrix may consist of a single hydrophilic polymer mentioned above or a mixture of several of them, chosen from the same family of hydrophilic polymers and preferably up to three of them.

In the context of the present invention, the families of hydrophilic polymers are defined by the following list:

natural polysaccharides,
cellulose derivatives,
polyvinylpyrrolidones,
polymers derived from acrylic acid and methacrylic acid and salts thereof,
aminoacid polymers.

Among the mixtures which may be mentioned in particular are mixtures of hydroxypropylcellulose and of hydroxypropylmethylcellulose and mixtures of hydroxypropylmethylcelluloses of different molecular weights.

One mixture which is particularly preferred consists of hydroxypropylmethylcelluloses of different molecular weights.

In order to promote a rapid increase in the volume of the pharmaceutical composition, with the hydrophilic polymers mentioned above, it is possible to use hydrophilic products and/or excipients capable of promoting the hydration of the swelling polymer matrices. Hydrophilic diluents such as lactose, mannitol, sorbitol or microcrystalline cellulose may be used for this purpose. Substances which allow faster wetting of the swelling polymer matrix or matrices may also be introduced, thereby facilitating the interaction between the components of this or these layers and the biological fluids. Examples of such substances are sodium lauryl sulfate, sodium ricinoleate, sodium tetradecylsulfate, sodium dioctyl sulfosulfonate, ketomagrocol, poloxamer, polysorbates or any other pharmacologically acceptable surfactant.

Two cases may be distinguished in the choice of excipients which modify the release of the active principle included in (a):

When the active principle and the carbon dioxide-generating system are in the same layer [(a)+(b)], the hydrophilic polymer(s) which form(s) the swelling hydrophilic matrix or matrices act(s) as modifiers of the release of the active principle. Consequently, a specific excipient which modifies the release of the active principle is not added to the swelling hydrophilic polymers.

When the active principle is in a layer [(a)] comprising no (b), the excipients modifying the release of the active principle are either hydrophilic polymers or lipid substances which may form a matrix, or a combination of both.

The hydrophilic polymers which may modify the release of the active principle may be chosen from those listed above as hydrophilic polymers forming a swelling matrix, to which may be added ethylcellulose, methylcellulose and acrylic copolymers among them those sold under the brand name Eudragit®.

The lipid substances may be chosen from hydrogenated castor oil, beeswax, carnauba wax, glyceryl trimyristate, glyceryl trilaurate, glyceryl tristearate, cetyl palmitate and glyceryl behenate.

The soluble and/or erodable material, one layer of which may consist of [lacuna], may be chosen from: soluble diluents such as lactose, mannitol, sorbitol, xylitol or polyalcohols, occasionally mixed with other hydrophilic diluents such as microcrystalline cellulose. Polymers such as hydroxyethylcellulose, carboxymethylcellulose, alginate, albumin, soluble starch or gelatin may be incorporated into this soluble and/or erodable layer up to a percentage of 25% by weight to control the rate of erosion and/or dissolution.

The technical preparation of the tablets may lead to the introduction:

of lubricants such as magnesium stearate, sodium stearylfumarate, stearic acid, glyceryl monostearate, polyoxyethylene glycols with a molecular weight of from 400 to 7 000 000, hydrogenated castor oil, glyceryl behenate and mono-, di- or trisubstituted glycerides, glidants such as colloidal silica or any other silica, and binders, buffers and absorbers, and also any other pharmaceutically acceptable additive.

According to preferred embodiments, the compositions of the invention may take the following different forms:
(1) A two-layer tablet, the first layer comprising the active principle and an excipient which modifies its release, and the second layer comprising a carbon dioxide generator in a swelling polymer matrix.

This type of tablet is represented in FIG. 1(i).
(2) A three-layer tablet, the first layer comprising the active principle and an excipient which modifies its release, and the two outer layers comprising a carbon dioxide generator in a swelling polymer matrix. The composition and size of the two outer layers may be identical or different.

This type of tablet is represented in FIG. 1(ii).
(3) A three-layer tablet, the outer layers comprising the active principle combined with an excipient which modifies its release and a carbon dioxide generator, the whole in a swelling polymer matrix, and the inner layer consisting of a soluble and/or erodable material and optionally of a carbon dioxide generator. The composition and size of the two outer layers may be identical or different.

This type of tablet is represented in FIG. 1 (iii).

The tablets of the invention may be produced in the following way: powders and/or granules are mixed together using the current production techniques, and thus with a production process which may be immediately transferred to the industrial scale.

The two-layer or three-layer pharmaceutical tablet is obtained according to tableting processes that are widely used by and known to those skilled in the art.

For example, the tablets may be produced using rotary presses capable of producing "multi-layer" tablets.

Normally, the working tableting force ranges from 7 to 50 kN (or kilonewtons) and two-layer or three-layer tablets are obtained in cylindrical, lenticular, spheroidal or ovoidal shape, making them easy to administer and swallow.

Depending on the amount of active principle which is conveyed, each layer of the tablet may have a different thickness ranging from 0.2 mm to 8 mm, but preferably from 1 mm to 4 mm.

A coating made of polymer materials may also be applied to the pharmaceutical composition for the purpose of providing a simple protection of the pharmaceutical composition. In this case, the coating should be soluble in acid and neutral solution.

The coating may be applied by conventional methods known to those skilled in the art, using organic or aqueous solutions.

The contents of the various compounds constituting a pharmaceutical composition according to the invention are generally chosen such that the relative density of this composition in the stomach is less than 1.00.

A pharmaceutical composition according to the invention usually comprises from 0.5% to 70% and preferably from 2% to 60% by weight of active principle, from 10% to 80% and preferably from 15% to 60% by weight of excipient which modifies the release of the active principle, from 10% to 75% and preferably from 15% to 60% by weight of at least one hydrophilic polymer and from 2.5% to 50% and preferably from 10% to 40% by weight of carbon dioxide-generating agent, the percentages being expressed relative to the total weight of the said composition.

The examples which follow illustrate the present invention.

EXAMPLE 1

Sustained-Release Floating Tablet Containing 3 Layers of Tiapride Hydrochloride

Two granules are prepared. For granule 1, Methocel® K100M, Avicel® PH102 and tartaric acid are dry-mixed and then granulated with water in a granulating blender and the granules obtained are then dried. The other components, magnesium stearate, Aerosile® 200 and monosodium carbonate are then dry-added and mixed. For granule 2, tiapride hydrochloride, Methocel® and Avicel® are dry-mixed and are then granulated with water in a granulating blender and the granules obtained are then dried. Magnesium stearate and Aerosile® are dry-added and mixed. 3-layer tablets are prepared, containing 250 mg of granule 1 in the first outer layer, 280 mg of granule 2 in the inner layer, which contains 100 mg of base tiapride in hydrochloride form, and 200 mg of granule 1 in the second outer layer.

| Granule 1: outer layers 1 and 3 | |
|---|---|
| Methocel ® K100M[1] | 45.6% |
| Avicel ® PH102[2] | 15.3% |
| Tartaric acid | 17.9% |
| Monosodium carbonate | 20.0% |
| Magnesium stearate | 1.0% |
| Aerosil ® 200[3] | 0.2% |
| | 100.0% |
| Granule 2: inner layer 2 | |
| Tiapride hydrochloride | 39.6% |
| Methocel ® K100M | 41.6% |
| Avicel ® PH101 | 17.6% |
| Aerosil ® 200 | 0.2% |
| Magnesium stearate | 1.0% |
| | 100.0% |

Figure 2:
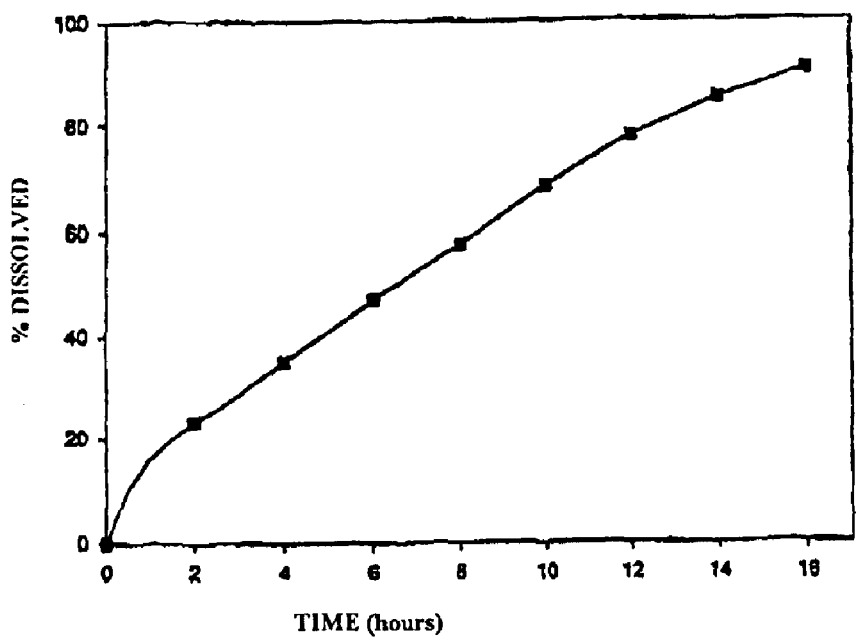
FIG. 2 represents the dissolution profile of tiapride hydrochloride formulated in a three-layer tablet according to the invention.

[1]hydroxypropylmethylcellulose sold by Dow Chemical Co.
[2]microcrystalline cellulose sold by Edward Mendell Co.
[3]colloidal silica sold by the company Degussa The in vitro dissolution is tested according to the following method:

The vane machine described by the European Pharmacopea is used. The stirring speed is 200 rpm. The UV absorbance is read continuously, by means of withdrawal using a peristaltic pump. The percentage of dissolved tiapride is determined as a function of time, by comparing the UV absorbance at 288 nm of the sample with that of a tiapride hydrochloride standard with a concentration of 0.222 mg/ml in the dissolution medium. The dissolution medium consists of 1000 ml of 0.01 M hydrochloric acid. The results are given in FIG. 2.

A controlled release of the tiapride hydrochloride is obtained.

EXAMPLE 2

Sustained-Release Floating 3-Layer Tablet of NS 49 in Hydrochloride Form 2 granules are prepared. Granule 1 is identical to that of the above example. Granule 2 is as described below. Three-layer tablets are prepared, containing 150 mg of granule 1 in the first outer layer, 100 mg of granule 2 in the inner layer, which contains 2 mg of NS 49 in hydrochloride form, and 100 mg of granule 1 in the 2nd outer layer.

| Granule 2: inner layer 2 | |
| --- | --- |
| NS 49 hydrochloride | 2.0% |
| Methocel ® K100M | 45.0% |
| Avicel ® PH101 | 51.8% |
| Aerosil ® 200 | 0.2% |
| Magnesium stearate | 1.0% |
| | 100.0% |

What is claimed is:

1. A controlled-release pharmaceutical composition with gastric residence comprising two or three layers and consisting essentially of:
   (a) an active principle combined with an excipient which modifies its release,
   (b) a carbon dioxide-generating system in a swelling hydrophilic polymer matrix consisting of a hydrophilic polymer chosen from the following families of hydrophilic polymers:
      natural polysaccharides,
      cellulose derivatives,
      polyvinylpyrrolidones,
      polymers derived from acrylic acid and methacrylic acid and salts thereof, or
      aminoacid polymers,
   or a mixture of 2 or 3 hyrdophilic polymers chosen from the same family wherein (a) and (b) are included in the same layer [(a)+(b)] or in separate layers ](a)[ and [(b)] and wherein multiple layers containing (a), (b) or (a) and (b) in the same tablet have the same or different compositions and dimensions, and
   (c) a hydrophilic excipient capable of promoting the hydration of swelling polymer matrices, chosen from lactose, mannitol, sorbitol, microcrystalline cellulose, sodium lauryl sulfate, sodium ricinoleate, sodium tetradecyl sulfate, sodium dioctyl sulfosulfonate, ketomagrocol, poloxamer and polysorbates.

2. A composition according to claim 1 wherein the carbon dioxide-generating system comprises at least one carbon dioxide-generating agent chosen from an alkali metal carbonate, an alkaline-earth metal carbonate and an alkali metal bicarbonate.

3. A composition according to claim 2 wherein the carbon dioxide-generating system comprises at least one carbon dioxide-generating agent and at least one acidic compound chosen from the group consisting of monocarboxylic acids, polycarboxylic acids and partial salts of polycarboxylic acids.

4. A composition according to claim 3 wherein the acidic compound is tartaric acid, succinic acid, citric acid or a partial salt thereof.

5. A composition according to claim 4 wherein the active principle is a benzamide.

6. A composition according to claim 4 wherein the active principle is an $\alpha_1$-antagonist.

7. A composition according to claim 4 wherein the active principle is captopril, furosemide, ursodeoxycholic acid, amoxicillin, (+)-α-aminomethyl-2-methoxy-5-sulfonamidobenzenemethanol or 3'-(2-amino-1-hydroxyethyl)-4'-fluoromethanesulfonanilide, or a salt thereof.

8. A composition according to claim 4 wherein the active principle is selected from the group consisting of amisulpride (D)-tartrate, (S)-(–)-amisulpride, (S)-(–)-amisulpride (D)-tartrate, tiapride hydrochloride, alfuzosine hydrochloride and 3'-(2-amino-1-hydroxyethyl)4'-fluoromethanesulfonanilide hydrochloride.

9. A composition according to claim 1 wherein the active principle is a benzamide.

10. A composition according to claim 1 wherein the active principle is an $\alpha_1$-antagonist.

11. A composition according to claim 1 wherein the active principle is captopril, furosemide, ursodeoxycholic acid, amoxicillin, (+)-α-aminomethyl-2-methoxy-5-sulfonamidobenzenemethanol or 3'-(2-amino-1-hydroxyethyl)-4'-fluoromethanesulfonanilide, or a salt thereof.

12. A composition according to claim 1 wherein the active principle is selected from the group consisting of amisulpride (D)-tartrate, (S)-(–)-amisulpride, (S)-(–)-amisulpride (D)-tartrate, tiapride hydrochloride, alfuzosine hydrochloride and 3'-(2-amino-1-hydroxyethyl)4'-fluoromethanesulfonanilide hydrochloride.

13. A composition according to claim 1 wherein the excipient which modifies the release of the active principle is a hydrophilic polymer chosen from the following families of hydrophilic polymers:
   natural polysaccharides,
   cellulose derivatives,
   polyvinylpyrrolidones,
   polymers derived from acrylic acid and methacrylic acid and salts thereof, or
   aminoacid polymers,
   or a mixture of 2 or 3 hydrophilic polymers chosen from the same family,
   or, when (a) and (b) are in separate layers, said excipient may further be a lipid substance chosen from hydrogenated castor oil, beeswax, carnauba wax, glyceryl trimyristate, glyceryl trilaurate, glyceryl tristearate, cetyl palmitate and glyceryl behenate, or a combination of a hydrophilic polymer and a lipid substance.

14. A composition according to claim 13 wherein the carbon dioxide-generating system comprises at least one carbon dioxide-generating agent which may be chosen from an alkali metal carbonate or alkaline-earth metal carbonate and an alkali metal bicarbonate.

15. A composition according to claim 14 wherein the carbon dioxide-generating system comprises at least one carbon dioxide-generating agent and at least one acidic compound chosen from the group consisting of monocarboxylic acids, polycarboxylic acids and partial salts of polycarboxylic acids.

16. A composition according to claim 15 wherein the acidic compound is tartaric acid, succinic acid, citric acid or a partial salt thereof.

17. A composition according to claim 16 wherein the active principle is a benzamide.

18. A composition according to claim 16 wherein the active principle is an $\alpha_1$-antagonist.

19. A composition according to claim 16 wherein the active principle is captopril, furosemide, ursodeoxycholic acid, amoxicillin, (+)-α-aminomethyl-2-methoxy-5-sulfonamidobenzenemethanol or 3'-(2-amino-1-hydroxyethyl)-4'-fluoromethanesulfonanilide, or a salt thereof.

20. A composition according to claim 16 wherein the active principle is selected from the group consisting of amisulpride (D)-tartrate, (S)-(–)-amisulpride, (S)-(–)-amisulpride (D)-tartrate, tiapride hydrochloride, alfuzosine hydrochloride and 3'-(2-amino-1-hydroxyethyl)-4'-fluoromethanesulfonanilide hydrochloride.

21. A composition according to claim 1 wherein the hydrophilic polymer is chosen from
- alginates, xantham gum, guar gum, gum arabic or carob gum,
- methylhydroxyethylcellulose, carboxymethylcellulose, sodium carboxymethylcellulose, calcium carboxymethylcellulose, hydroxypropylcellulose or hydroxypropylmethylcellulose,
- polyacrylates, or polylysines.

22. A composition according to claim 21 wherein the excipient which modifies the release of the active principle is a hydrophilic polymer chosen from the following families of hydrophilic polymers:
- natural polysaccharides,
- cellulose derivatives,
- polyvinylpyrrolidones,
- polymers derived from acrylic acid and methacrylic acid and salts thereof, or
- aminoacid polymers, or a mixture of 2 or 3 hydrophilic polymers chosen from the same family,
or, when (a) and (b) are in separate layers, said excipient may further be a lipid substance chosen from hydrogenated castor oil, beeswax, carnauba wax, glyceryl trimyristate, glyceryl trilaurate, glyceryl tristearate, cetyl palmitate and glyceryl behenate, or a combination of a hydrophilic polymer and a lipid substance.

23. A composition according to claim 22 wherein the carbon dioxide-generating system comprises at least one carbon dioxide-generating agent chosen from an alkali metal carbonate or alkaline-earth metal carbonate and an alkali metal bicarbonate.

24. A composition according to claim 23 wherein the carbon dioxide-generating system comprises at least one carbon dioxide-generating agent and at least one acidic compound chosen from the group consisting of monocarboxylic acids, polycarboxylic acids and partial salts of polycarboxylic acids.

25. A composition according to claim 24 wherein the acidic compound is tartaric acid, succinic acid, citric acid or a partial salt thereof.

26. A composition according to claim 25 wherein the active principle is a benzamide.

27. A composition according to claim 25 wherein the active principle is an $\alpha_1$-antagonist.

28. A composition according to claim 25 wherein the active principle is captopril, furosemide, ursodeoxycholic acid, amoxicillin, (+)-α-aminomethyl-2-methoxy-5-sulfonamidobenzenemethanol or 3'-(2-amino-1-hydroxyethyl)-4'-fluoromethanesulfonanilide, or a salt thereof.

29. A composition according to claim 25 wherein the active principle is selected from the group consisting of amisulpride (D)-tartrate, (S)-(−)-amisulpride, (S)-(−)-amisulpride (D)-tartrate, tiapride hydrochloride, alfuzosine hydrochloride and 3'-(2-amino-1-hydroxyethyl)-4'-fluoromethanesulfonanilide hydrochloride.

* * * * *